US 8,242,310 B2

(12) United States Patent
Saindane et al.

(10) Patent No.: US 8,242,310 B2
(45) Date of Patent: Aug. 14, 2012

(54) PROCESSES FOR THE PREPARATION OF AMINOSULFONE COMPOUNDS

(75) Inventors: Manohar T. Saindane, Monmouth Junction, NJ (US); Chuansheng Ge, Belle Mead, NJ (US)

(73) Assignee: Celgene Corporation, Summit, NJ (US)

( * ) Notice: Subject to any disclaimer, the term of this patent is extended or adjusted under 35 U.S.C. 154(b) by 458 days.

(21) Appl. No.: 12/556,479

(22) Filed: Sep. 9, 2009

(65) Prior Publication Data

US 2010/0168475 A1 Jul. 1, 2010

Related U.S. Application Data

(60) Provisional application No. 61/095,902, filed on Sep. 10, 2008.

(51) Int. Cl.
*C07C 321/00* (2006.01)
*C07C 211/00* (2006.01)

(52) U.S. Cl. ........................................ 564/340; 564/336

(58) Field of Classification Search .................... None
See application file for complete search history.

(56) References Cited

OTHER PUBLICATIONS

Kirk-Othmer Encyclopedia of Chemical Technology Copyright© 2002 by John Wiley & Sons, Inc., pp. 95-147, Article Online Posting Date: Aug. 16, 2002.*
Rouhi, "The Right Stuff, from research and development to the clinic, getting drug crystals right is full of pitfalls", Chemical & Engineering News, Feb. 24, 2003, pp. 32-35.*
"Crystallization and Precipitation" in Ullmann's Encyclopedia of Industrial Chemistry, Copyright© 2002 by Wiley-VCH Verlag GmbH & Co. KGaA , pp. 1-51.*

* cited by examiner

*Primary Examiner* — Karl J Puttlitz
(74) *Attorney, Agent, or Firm* — Jones Day

(57) ABSTRACT

Processes for synthesizing aminosulfone compounds are provided. Aminosulfone compounds obtained using methods provided herein are useful in production or synthesis of isoindoline based PDE 4 modulators.

24 Claims, No Drawings

PROCESSES FOR THE PREPARATION OF AMINOSULFONE COMPOUNDS

This application claims priority to U.S. provisional application No. 61/095,902, filed Sep. 10, 2008, the entirety of which is incorporated herein by reference.

1. FIELD

Provided are processes for the preparation of an aminosulfone compound, e.g., 2-(3-ethoxy-4-methoxyphenyl)-1-(methanesulfonyl)-eth-2-ylamine. The compound can be used in making sulfone containing PDE 4 modulators, for example, S-enantiomer form of 2-[1-(3-ethoxy-4-methoxyphenyl)-2-methylsulfonylethyl]-4-acetylaminoisoindoline-1,3-dione.

2. BACKGROUND

Enhanced or unregulated production of tumor necrosis factor α (TNF-α) has been implicated in inflammatory, allergic, and autoimmune diseases. It has been shown that Adenosine 3',5'-cyclic monophosphate (cAMP) plays a role in TNF-α production. Elevation of cAMP in inflammatory leukocytes inhibits their activation and the subsequent release of inflammatory mediators, including TNF-α. The primary cellular mechanism for the inactivation of cAMP is the breakdown of cAMP by a family of isoenzymes referred to as cyclic nucleotide phosphodiesterases (PDE). The inhibition of PDE, in particular type IV PDE (PDE4), is effective in the inhibition of TNF-α release.

For example, 2-[1-(3-ethoxy-4-methoxyphenyl)-2-methylsulfonylethyl]-4-acetylaminoisoindoline-1,3-dione is a PDE4 inhibitor that is currently under investigation as an anti-inflammatory for the treatment of a variety of conditions, including asthma, chronic obstructive pulmonary disease, psoriasis and other allergic, autoimmune and rheumatologic conditions. S-enantiomer form of 2-[1-(3-ethoxy-4-methoxyphenyl)-2-methylsulfonylethyl]-4-acetylaminoisoindoline-1,3-dione can be prepared by reacting (S)-aminosulfone 1 with intermediate 2.

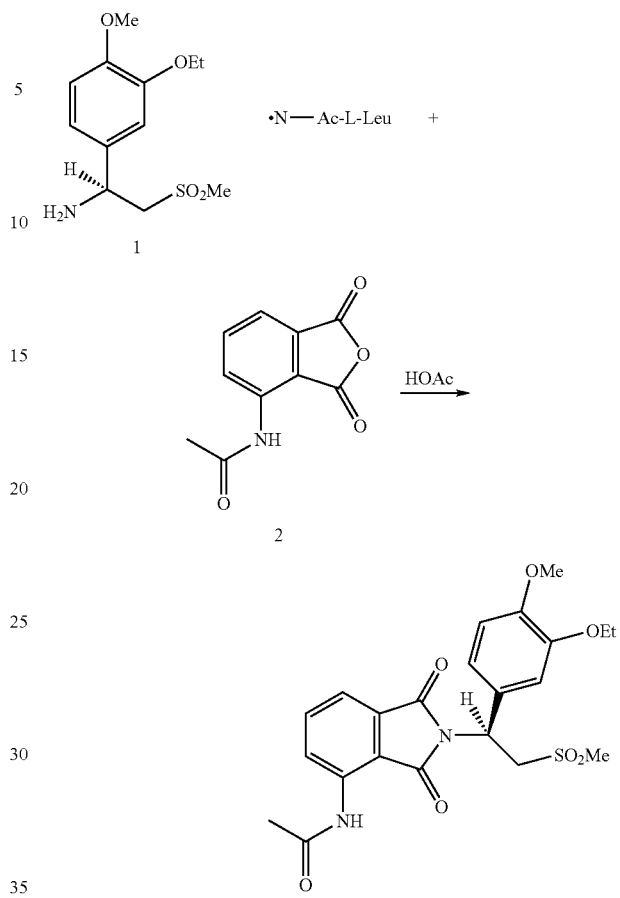

Currently, (S)-aminosulfone 1 is prepared by converting 3-ethoxy-4-methoxybenzaldehyde 3 to racemic aminosulfone 5 followed by resolution with N—Ac-L-Leu.

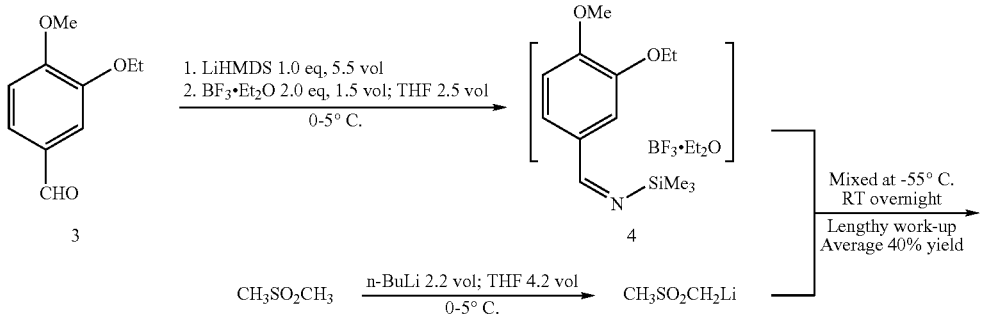

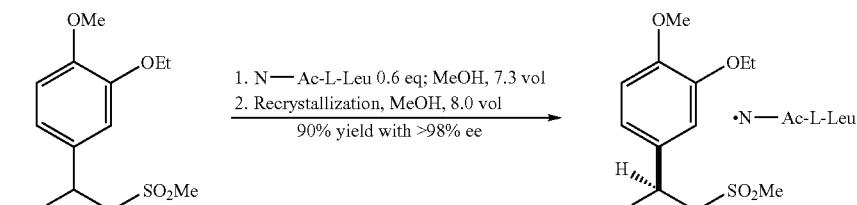

3

The current procedure for preparing racemic aminosulfone 5, as shown in the above scheme, is inefficient due to its long process cycle time and low yield. Alternative methods for the preparation of racemic aminosulfone 5, particularly for manufacturing scale production, are thus desirable.

3. SUMMARY

Provided are processes for the preparation of aminosulfone compounds. In one embodiment, provided is a process for preparing an aminosulfone compound of Formula I:

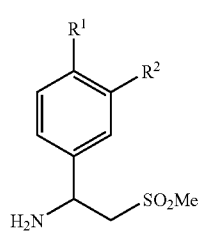

(I)

or a salt, solvate including a hydrate, stereoisomer, or polymorph thereof, wherein $R^1$ and $R^2$ are defined herein elsewhere.

In one embodiment, the aminosulfone compound is a compound of Formula (I), wherein $R_1$ is methoxy and $R_2$ is ethoxy, i.e., 2-(3-ethoxy-4-methoxyphenyl)-1-(methanesulfonyl)-eth-2-ylamine. Such an aminosulfone compound can be used to provide, for example, 2-[1-(3-ethoxy-4-methoxyphenyl)-2-methylsulfonylethyl]-4-acetylaminoisoindoline-1,3-dione in further processes.

4. DETAILED DESCRIPTION

4.1 Definition

As used herein and unless otherwise indicated, the term "process(es)" provided herein refers to the methods disclosed herein which are useful for preparing a compound provided herein. Modifications to the methods disclosed herein (e.g., starting materials, reagents, protecting groups, solvents, temperatures, reaction times, purification) are also encompassed by the present disclosure.

As used herein, and unless otherwise indicated, the term "adding," "reacting," "treating," or the like means contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order. They can be added in the presence or absence of heat and can optionally be added under an inert atmosphere. "Reacting" can refer to in situ formation or intramolecular reaction where the reactive groups are in the same molecule.

As used herein, and unless otherwise indicated, a reaction that is "substantially complete" or is driven to "substantial completion" means that the reaction contains more than about 80% by percent yield, in one embodiment more than about 90% by percent yield, in another embodiment more than about 95% by percent yield, and in another embodiment more than about 97% by percent yield of the desired product.

As used herein, and unless otherwise indicated, the term "salt" includes, but is not limited to, salts of acidic or basic groups that may be present in the compounds disclosed herein. Compounds that are basic in nature are capable of forming a wide variety of salts with various inorganic and organic acids. The acids that may be used to prepare salts of such basic compounds are those that form salts comprising anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate. Compounds that include an amino group also can form salts with various amino acids, in addition to the acids mentioned above. Compounds that are acidic in nature are capable of forming base salts with various cations. Non-limiting examples of such salts include alkali metal or alkaline earth metal salts and, in some embodiments, calcium, magnesium, sodium, lithium, zinc, potassium, and iron salts. Compounds that are acidic in nature are also capable of forming base salts with compounds that include an amino group.

As used herein, and unless otherwise indicated, the term "hydrate" means a compound or a salt thereof, that further includes a stoichiometric or non-stoichiometric amount of water bound by non-covalent intermolecular forces.

As used herein, and unless otherwise indicated, the term "solvate" means a solvate formed from the association of one or more solvent molecules to a compound. The term "solvate" includes hydrates (e.g., mono-hydrate, dihydrate, trihydrate, tetrahydrate, and the like).

As used herein, and unless otherwise indicated, the term "polymorph" means solid crystalline forms of a compound or complex thereof. Different polymorphs of the same compound can exhibit different physical, chemical and/or spectroscopic properties.

As used herein, and unless otherwise indicated, the term "amino" or "amino group" means a monovalent group of the formula —$NH_2$, —NH(alkyl), —NH(aryl), —N(alkyl)$_2$, —N(aryl)$_2$ or —N(alkyl)(aryl).

As used herein, and unless otherwise indicated, acronyms or symbols for groups or reagents have the following definition: HPLC=high performance liquid chromatography; TFA=trifluoroacetic acid; THF=tetrahydrofuran; $CH_3CN$=acetonitrile; HOAc=acetic acid; DCM=dichloromethane; Lewis acids=$Et_2AlCl$, $EtAlCl_2$, $BF_3$, $SnCl_4$, $AlCl_3$, Ti (isopropoxide)$_4$ and $TiCl_4$.

As used herein, and unless otherwise indicated, the term "substituted" or "substitution," when used to describe a chemical structure or moiety, refers to a derivative of that structure or moiety wherein one or more of its hydrogen atoms is replaced with a substituent such as, but not limited to: alkyl, alkenyl, alkynyl, and cycloalkyl; alkoxyalkyl; aroyl; halo; haloalkyl (e.g., trifluoromethyl); heterocycloalkyl; haloalkoxy (e.g., trifluoromethoxy); hydroxy; alkoxy; cycloalkyloxy; heterocylooxy; oxo; alkanoyl; aryl; heteroaryl (e.g., indolyl, imidazolyl, furyl, thienyl, thiazolyl, pyrrolidyl, pyridyl, and pyrimidyl); arylalkyl; alkylaryl; heteroaryl; heteroarylalkyl; alkylheteroaryl; heterocyclo; heterocycloalkyl-alkyl; aryloxy, alkanoyloxy; amino; alkylamino; arylamino; arylalkylamino; cycloalkylamino; heterocycloamino; mono- and di-substituted amino; alkanoylamino; aroylamino; aralkanoylamino; aminoalkyl; carbamyl (e.g., $CONH_2$); substituted carbamyl (e.g., CONH-alkyl, CONH-aryl, CONH-arylalkyl or instances where there are two substituents on the nitrogen); carbonyl; alkoxycarbonyl; carboxy; cyano; ester; ether; guanidino; nitro; sulfonyl; alkylsulfonyl; arylsulfonyl; arylalkylsulfonyl; sulfonamido (e.g., $SO_2NH_2$); substituted sulfonamido; thiol; alkylthio; arylthio; arylalkylthio; cycloalkylthio; heterocyclothio; alkylthiono;

arylthiono; and arylalkylthiono. In some embodiments, a substituent itself may be substituted with one or more chemical moieties such as, but not limited to, those described herein.

As used herein, and unless otherwise indicated, the term "about" is used to specify that the values given are approximate. For example, the term "about," where it is used in connection with reaction temperatures, denotes that the temperature deviations within 30%, 25%, 20%, 15%, 10%, or 5% are encompassed by the temperature indicated. Similarly, the term "about," where it is used in connection with reaction time, denotes that the time period deviations within 30%, 25%, 20%, 15%, 10%, or 5% are encompassed by the time period indicated.

If the stereochemistry of a structure or a portion thereof is not indicated, e.g., with bold or dashed lines, the structure or portion thereof is to be interpreted as encompassing all enantiomerically pure, enantiomerically enriched, diastereomerically pure, diastereomerically enriched, and racemic mixtures of the compounds.

The disclosure can be understood more fully by reference to the following detailed description and illustrative examples, which are intended to exemplify non-limiting embodiments.

4.2 Processes

Provided herein are processes for the preparation of aminosulfone compounds. In one embodiment, provided is a process for preparing an aminosulfone compound of Formula (I):

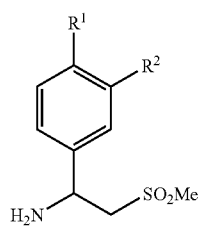

or a salt, solvate including a hydrate, stereoisomer, or polymorph thereof, wherein $R^1$ and $R^2$ are each independently hydrogen, substituted or unsubstituted $(C_1-C_6)$alkyl, substituted or unsubstituted $(C_1-C_6)$alkoxy, $(C_3-C_{18})$cycloalkyl, $(C_3-C_6)$cycloalkoxy, cyano, or $(C_3-C_{18})$cycloalkyl-$(C_1-C_6)$alkoxy, comprising the steps of:

(1) reacting an aldehyde of Formula (II):

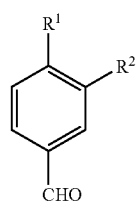

with hydroxylamine, or a salt thereof, to form a nitrile of Formula (III):

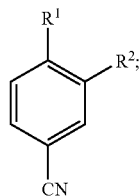

(2) reacting the nitrile of Formula (III) with $LiCH_2SO_2CH_3$, to form an enamine of Formula (IV):

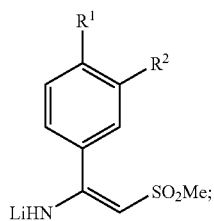

and (3) reducing the enamine of Formula (IV) to form the compound of Formula I, or a salt thereof.

In step (1), the reaction between the aldehyde of Formula (II) and hydroxylamine, or a salt thereof, can occur in a solvent such as, but not limited to, ethyl acetate, acetone, methyl ethyl ketone, diethyl ether, tetrahydrofuran, acetonitrile, dichloromethane, chloroform, N-methylpyrrolidinone, dimethyl formamide, dimethyl sulfoxide, formic acid, acetic acid, and mixtures thereof. In one embodiment, the solvent is acetonitrile. In another embodiment, the solvent is formic acid. In another embodiment, the solvent is acetic acid.

In step (1), the reaction temperature can be between about 10° C. and about 90° C. In one embodiment, the reaction temperature is between about 65° C. and about 85° C.

In step (1), the reaction time can vary from about 1 to about 24 hours, depending on the reaction temperature. In general, the higher the reaction temperature, the shorter is the reaction time. In one embodiment, the reaction time is about 5 hours where the reaction temperature is between about 65° C. and about 85° C.

In one embodiment, the reaction between the aldehyde of Formula (II) and hydroxylamine, or a salt thereof, occurs in acetonitrile at a temperature between about 65° C. and about 85° C. for about 5 hours. In another embodiment, the reaction between the aldehyde of Formula (II) and hydroxylamine, or a salt thereof, occurs in formic acid at a temperature between about 65° C. and about 85° C. for about 5 hours. In a further embodiment, the reaction between the aldehyde of Formula (II) and hydroxylamine, or a salt thereof, occurs in acetic acid at a temperature between about 65° C. and about 85° C. for about 5 hours.

In step (2), the reaction between the nitrile of Formula (III) and $LiCH_2SO_2CH_3$ can occur in a solvent such as, but not limited to, diethyl ether, tetrahydrofuran, N-methyl pyrrolidinone, MTBE, glyme, diglyme, toluene, xylene, hexanes, and mixtures thereof. In one embodiment, the solvent is a mixture of tetrahydrofuran and hexanes.

In step (2), the reaction temperature can be between about 0° C. and about 60° C. In one embodiment, the reaction temperature is between about 0° C. and about 25° C.

In step (2), the reaction time can vary from about 1 to about 24 hours, depending on the reaction temperature. In general, the higher the reaction temperature, the shorter is the reaction time. In one embodiment, the reaction time is about 2 hours at a reaction temperature between about 0° C. and about 25° C.

In another embodiment, the reaction between the nitrile of Formula (III) and $LiCH_2SO_2CH_3$ occurs in tetrahydrofuran and hexanes at a temperature between about 0° C. and about 25° C. for about 2 hours.

The $LiCH_2SO_2CH_3$ in step (2) can be prepared by reacting dimethylsulfone with butyllithium. The reaction between dimethylsulfone and butyllithium can occur in a solvent such as, but not limited to, diethyl ether, tetrahydrofuran, N-methylpyrrolidinone, MTBE, glyme, diglyme, toluene, xylene, hexanes, and mixtures thereof. In one embodiment, the solvent is a mixture of tetrahydrofuran and hexanes.

The reaction between dimethylsulfone and butyllithium can occur at a temperature between about 0° C. and about 20° C. In one embodiment, the reaction temperature is between about 0° C. and about 5° C.

The reaction time between dimethylsulfone and butyllithium can vary from about 1 to about 24 hours, depending on the reaction temperature. In general, the higher the reaction temperature, the shorter is the reaction time. In one embodiment, the reaction time is about 2 hours at a reaction temperature between about 0° C. and about 5° C.

In one embodiment, the $LiCH_2SO_2CH_3$ in step (2) is prepared by reacting dimethylsulfone with butyllithium in tetrahydrofuran and hexanes at a temperature between about 0° C. and about 5° C. for about 2 hours.

Any reducing agent known in the art for reducing an enamine to an amine can be used for the reduction in step (3). In one embodiment, the reducing agent is $NaBH(OAc)_3$. In another embodiment, the reducing agent is $NaBH_4$.

The reduction in step (3) can occur in the presence of an acid source such as, but not limited to, acetic acid, methanesulfonic acid, trifluoroacetic acid, 4-(trifluoromethyl)benzoic acid, p-toluenesulfonic acid, hydrochloric acid, nitric acid, sulfuric acid, phosphoric acid, and mixtures thereof. In one embodiment, the acid source is trifluoroacetic acid. In another embodiment, the acid source is acetic acid. In another embodiment, the acid source is a mixture of trifluoroacetic acid and acetic acid.

The reduction in step (3) can occur in a solvent such as, but not limited to, ethyl acetate, diethyl ether, tetrahydrofuran, acetic acid, acetonitrile, N-methylpyrrolidinone, dimethylformamide, dimethyl sulfoxide, hexanes, and mixtures thereof. In one embodiment, the solvent is a mixture of tetrahydrofuran and hexanes.

The reduction in step (3) can occur at a temperature between about 0° C. to about 25° C. In one embodiment, the reduction occurs at a temperature between about 0° C. to about 5° C. The reduction is generally performed until the reaction is substantially complete. In another embodiment, the reduction is performed for at least about 1 hour at a temperature between about 0° C. to about 5° C.

In one embodiment, the reduction in step (3) occurs at a temperature between about 0° C. to about 5° C. for about 1 hour in tetrahydrofuran and hexanes in the presence of NaBH(OAc)$_3$ and trifluoroacetic acid. In another embodiment, the reduction in step (3) occurs at a temperature between about 0° C. to about 5° C. for about 1 hour in tetrahydrofuran and hexanes in the presence of $NaBH_4$ and acetic acid. In another embodiment, the reduction in step (3) occurs at a temperature between about 0° C. to about 5° C. for about 1 hour in tetrahydrofuran and hexanes in the presence of $NaBH_4$, trifluoroacetic acid and acetic acid.

In processes where the reduction in step (3) forms a salt of Formula (I), such as a borate salt, the salt is further hydrolyzed to form the compound of Formula (I).

The hydrolysis can occur in the presence of an acid catalyst such as, but not limited to, trifluoroacetic acid, 4-(trifluoromethyl)benzoic acid, p-toluenesulfonic acid, methanesulfonic acid, acetic anhydride, and Lewis acids (e.g., $Et_2AlCl$, $EtAlCl_2$, $BF_3$, $SnCl_4$, $AlCl_3$, Ti (isopropoxide)$_4$ and $TiCl_4$).

The hydrolysis can be a basic hydrolysis. Non-limiting examples of bases include NaOH, KOH, LiOH, and $Ca(OH)_2$. In one embodiment, the base source is NaOH.

The hydrolysis can occur at a temperature between about 0° C. to about 80° C. In one embodiment, the reaction occurs at a temperature between about 0° C. to about 60° C. The hydrolysis is generally performed until the reaction is substantially complete. In one embodiment, the reaction is performed for at least about 1 hour at a temperature between about 0° C. to about 60° C.

In another embodiment, the hydrolysis occurs at a temperature between about 0° C. to about 60° C. for about 1 hour in the presence of NaOH.

The aminosulfone compounds obtained using the methods described herein may be used in further processes to provide various compounds described in, for example, U.S. Pat. Nos. 6,667,316 and 6,692,940, the entireties of which are incorporated herein by reference.

In one embodiment, the aminosulfone compound obtained by the methods provided herein is a compound of Formula (I) wherein $R^1$ and $R^2$ are both $(C_1-C_6)$alkoxy. In another embodiment, the aminosulfone compound obtained by the methods provided herein is a compound of Formula (I) wherein $R^1$ and $R^2$ are both $(C_1-C_6)$alkyl. In another embodiment, the aminosulfone compound obtained by the methods provided herein is a compound of Formula (I) wherein one of $R^1$ and $R^2$ is $(C_1-C_6)$alkoxy, and the other of $R^1$ and $R^2$ is $(C_1-C_6)$alkyl. In another embodiment, the aminosulfone compound obtained by the methods provided herein is a compound of Formula (I) wherein one of $R^1$ and $R^2$ is $(C_1-C_6)$alkoxy, and the other of $R^1$ and $R^2$ is $(C_3-C_6)$cycloalkoxy.

In one embodiment, $R^1$ is methoxy and $R^2$ is ethoxy, i.e., the compound obtained by using the methods provided herein is 2-(3-ethoxy-4-methoxyphenyl)-1-(methanesulfonyl)-eth-2-ylamine. The compound may be used to further provide, for example, 2-[1-(3-ethoxy-4-methoxyphenyl)-2-methylsulfonylethyl]-4-acetylaminoisoindoline-1,3-dione, or a salt, solvate, or stereoisomer thereof, using methods known in the art or described herein elsewhere.

5. EXAMPLES

5.1 3-Ethoxy-4-Methoxybenzonitrile

5.1.1 Method 1

3-Ethoxy-4-methoxybenzaldehyde (1000 g, 5.54 moles, from Aldrich Chemicals, Milwaukee, Wis.) and hydroxylamine HCl (462.5 g, 6.6 moles, from Aldrich Chemicals, Milwaukee, Wis.) were charged to a 12 L three-necked flask at room temperature, followed by the addition of acetonitrile (5 L, from Fisher Scientific, Pittsburgh, Pa.). The reaction mixture was stirred at room temperature for 15-20 minutes, and a latent endotherm (~5-15° C. below room temperature) was observed. After the endotherm had subsided, the reaction mixture was warmed to 65-72° C. The reaction mixture was further heated to reflux at 78-84° C. After 2-3 hours of reflux, the reaction mixture was cooled to room temperature, and added with 1 L of deionized water. 3.5-4.0 L of acetonitrile from the reaction mixture was distilled off under vacuum. The concentrated residue was diluted with 4 L of deionized water, and stirred at room temperature for 1-2 hours. The mixture was then filtered at room temperature under vacuum. The filtered solid was washed with 3-4 L of deionized water. The solid was dried in a tray at 30-32° C. for 24-36 hours under a pressure of 100-125 mm Hg. The yield of 3-ethoxy-4-methoxybenzonitrile was found to be 940 g (95.5%) based on 1000 g input of 3-ethoxy-4-methoxybenzaldehyde (HPLC indicated 99.2% purity by peak area).

5.1.2 Method 2

Alternatively, 3-ethoxy-4-methoxybenzonitrile was prepared similarly according to the procedure described in Section 5.1.1 above, except that acetonitrile was replaced with formic acid (from Aldrich Chemicals, Milwaukee, Wis.). The yield of 3-ethoxy-4-methoxybenzonitrile was found to be 90%.

5.1.3 Method 3

Alternatively, 3-ethoxy-4-methoxybenzonitrile was prepared similarly according to the procedure described in Section 5.1.1 above, except that acetonitrile was replaced with acetic acid (from Aldrich Chemicals, Milwaukee, Wis.). The yield of 3-ethoxy-4-methoxybenzonitrile was found to be 81% and 70% based on 100 g and 500 g input of 3-ethoxy-4-methoxybenzaldehyde, respectively.

5.2 2-(3-Ethoxy-4-Methoxyphenyl)-1-(Methanesulfonyl)-Eth-2-Ylamine from 3-Ethoxy-4-Methoxybenzonitrile 5.2.1 Method 1

Dimethylsulfone (191.1 g, 2.03 moles, from Aldrich Chemicals, Milwaukee, Wis.) and tetrahydrofuran (1.65 L, from Aldrich Chemicals, Milwaukee, Wis.) were charged to a 12 L three-necked flask at room temperature. The mixture was cooled to 0-5° C. n-BuLi (750 ml of 2.5M solution in hexanes, from Aldrich Chemicals, Milwaukee, Wis.) was added to the flask at a rate such that the reaction mixture was maintained at 0-5° C. A line rinse with 150 ml tetrahydrofuran followed. The mixture was stirred at 0-5° C. for 60-70 minutes. 3-ethoxy-4-methoxybenzonitrile (300.0 g, 1.69 moles, in 750 ml tetrahydrofuran) was then charged to the flask at a rate such that the reaction mixture was maintained at 0-5° C. A line rinse with 300 ml tetrahydrofuran followed. The mixture was stirred at 0-5° C. for another 10-15 minutes. After warming to room temperature, the reaction mixture was stirred at room temperature for 1.5-2 hours, while purged with nitrogen. $NaBH_4$ (83.1 g, 2.20 moles, from Aldrich Chemicals, Milwaukee, Wis.) and 150 ml of tetrahydrofuran were then charged to the reaction mixture. The reaction mixture was stirred at 0-5° C. for 15-30 minutes. HOAc (450 ml, 7.83 moles, from Fisher Scientific, Pittsburgh, Pa.) was charged to the flask at a rate such that the reaction mixture was maintained at 0-5° C. The mixture was stirred at 0-5° C. for an additional 2-3 hours. The mixture was then charged with 2.25 L of NaOH (2.5N, pH 12 to 13, from Fisher Scientific, Pittsburgh, Pa.), and stirred at 0-5° C. for another 15-30 minutes. After warming to room temperature, the reaction mixture was heated to reflux at about 60° C. After reflux for 12-14 hours, the mixture was cooled to 35-40° C., and 3.0 L of water was added. The mixture was further cooled to 0-5° C. over a period of 1.5-2 hours. The mixture was filtered under vacuum, and the filtered solid was washed with 2 L of deionized water. The solid was dried in a tray at 50-55° C. under vacuum. The yield of 2-(3-ethoxy-4-methoxyphenyl)-1-(methanesulfonyl)-eth-2-ylamine was found to be 352 g (76.1%) based on a 300 g input of 3-ethoxy-4-methoxybenzonitrile (HPLC indicated 99.74% purity by peak area).

5.2.2 Method 2

Alternatively, 2-(3-ethoxy-4-methoxyphenyl)-1-(methanesulfonyl)-eth-2-ylamine was prepared similarly according to the procedure described in Section 5.2.1 above, except that trifluoroacetic acid was added together with $NaBH_4$, as described in the following.

Dimethylsulfone (14.1 g, 150 mmoles, from Aldrich Chemicals) and tetrahydrofuran (55 ml, from Aldrich Chemicals) were charged to a three-necked RBF at room temperature. The mixture was cooled to 5-10° C. n-BuLi (55 ml of 2.5M solution in hexanes, from Aldrich Chemicals) was added to the flask at a rate such that the reaction mixture was maintained at 5-10° C. A line rinse with 11 ml tetrahydrofuran followed. The mixture was stirred at 0-5° C. for 80 minutes. 3-Ethoxy-4-methoxybenzonitrile (22.2 g, 125 mmoles, in 45 ml tetrahydrofuran) was then charged to the flask at a rate such that the reaction mixture was maintained at 0-5° C. A line rinse with 11 ml tetrahydrofuran followed. The mixture was stirred at 0-5° C. for another 10-15 minutes. After warming to room temperature, the reaction mixture was stirred for another 1.5-2 hours and then transferred to a 1 L three-necked RBF containing a suspension of $NaBH_4$ (6.1 g, 163 mmoles, from Acros) in 90 ml of tetrahydrofuran maintained at −10-0° C. A line rinse with 11 ml tetrahydrofuran followed. The reaction mixture was stirred at 0-5° C. for 30 minutes. TFA (43.3 ml, 563 mmoles, from Aldrich Chemicals) was charged to the flask at a rate such that the reaction mixture was maintained at 0-5° C. The mixture was stirred at 0-5° C. for 40 minutes and an additional 15 hours at ambient temperature. The mixture was then charged with 22.3 ml of DI water over 5 minutes at 15-20° C. The mixture was stirred at ambient temperature for 4 hours. Aq. NaOH (10N, 40 ml) was charged to the flask over 10-15 minutes at 45-50° C. The mixture was stirred at 45-50° C. for 2 hours, at 60° C. for 1.5 hours, at ambient overnight and 0-5° C. for 75 minutes. The mixture was clarified at 0-5° C. and the filtrate was concentrated on a Rotovap. The residual material was charged with DI water (110 ml) and Reagent alcohol (110 ml) and stirred at 0-5° C. for 2 hours. The mixture was filtered under vacuum, and the filtered solid was washed with cold Reagent alcohol (3×22 ml) followed by DI water until pH of the wash reached about 8. The solid was air dried, yielding 24.1 g (70.5%) of 2-(3-ethoxy-4-methoxyphenyl)-1-(methanesulfonyl)-eth-2-ylamine (HPLC indicated 96.78% purity by peak area).

5.2.3 Method 3

Alternatively, 2-(3-ethoxy-4-methoxyphenyl)-1-(methanesulfonyl)-eth-2-ylamine was prepared similarly according to the procedure described in Section 5.2.1 above, except that $NaBH_4$ was replaced with $NaBH(OAc)_3$ (from Aldrich Chemicals, Milwaukee, Wis.). Instead of $NaBH_4$, 2.0 equiv. of $NaBH(OAc)_3$ and 7.0 equiv. of trifluoroacetic acid were added to the reaction mixture. The reaction mixture was stirred at room temperature for 12-24 hours. The reaction was quenched with NaOH. The mixture was then filtered under vacuum, and the filtered solid was washed with 2 L of deionized water. The solid was dried in a tray at 50-55° C. under vacuum. The yield of 2-(3-ethoxy-4-methoxyphenyl)-1-(methanesulfonyl)-eth-2-ylamine was found to be 70% based on a 9 g input of 3-ethoxy-4-methoxybenzonitrile.

Alternatively, 2-(3-ethoxy-4-methoxyphenyl)-1-(methanesulfonyl)-eth-2-ylamine was isolated by extraction with DCM. The yield of 2-(3-ethoxy-4-methoxyphenyl)-1-(methanesulfonyl)-eth-2-ylamine by extraction was found to be 90% based on a 50 g input of 3-ethoxy-4-methoxybenzonitrile.

All of the references disclosed herein are incorporated by reference in their entireties. The embodiments described herein are intended to be merely exemplary, and those skilled in the art will recognize, or will be able to ascertain using no more than routine experimentation, numerous equivalents of specific compounds, materials, and procedures. All such equivalents are considered to be within the scope of the subject matter claimed and are encompassed by the appended claims.

What is claimed is:

1. A process for preparing a compound of Formula (I):

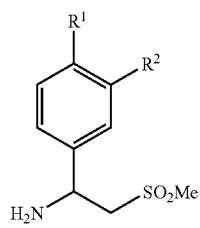

or a salt, or stereoisomer thereof, wherein $R^1$ and $R^2$ are each independently hydrogen, substituted or unsubstituted ($C_1$-$C_6$)alkyl, substituted or unsubstituted ($C_1$-$C_6$)alkoxy, ($C_3$-$C_{18}$)cycloalkyl, cyano, or ($C_3$-$C_{18}$)cycloalkyl-($C_1$-$C_6$)alkoxy, comprising the steps of:

(1) reacting a nitrile of Formula (III):

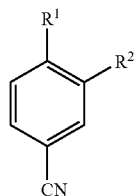

with $LiCH_2SO_2CH_3$, to form an enamine of Formula (IV):

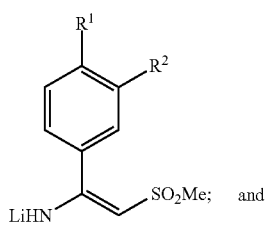

(2) reducing the enamine of Formula (IV) to form the compound of Formula (I) or a salt thereof.

2. The process of claim 1, wherein the nitrile of Formula (III) is formed by reacting an aldehyde of Formula (II):

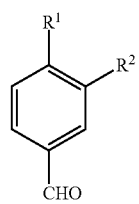

with hydroxylamine, or a salt thereof.

3. The process of claim 2, wherein the reaction between the aldehyde of Formula (II) and hydroxylamine, or a salt thereof, occurs in a solvent, wherein the solvent is ethyl acetate, acetone, methyl ethyl ketone, diethyl ether, tetrahydrofuran, acetonitrile, dichloromethane, chloroform, N-methylpyrrolidinone, dimethyl formamide, dimethyl sulfoxide, formic acid, acetic acid, and a combination thereof.

4. The process of claim 2, wherein the reaction between the aldehyde of Formula (II) and hydroxylamine, or a salt thereof, occurs at a temperature between about 10° C. and about 90° C.

5. The process of claim 1, wherein $LiCH_2SO_2CH_3$ is prepared by reacting $Me_2SO_2$ with n-BuLi.

6. The process of claim 5, wherein the reaction between $Me_2SO_2$ and n-BuLi occurs in a solvent, wherein the solvent is diethyl ether, tetrahydrofuran, N-methylpyrrolidinone, MTBE, glyme, diglyme, toluene, xylene, hexanes, or a combination thereof.

7. The process of claim 5, wherein the reaction between $Me_2SO_2$ and n-BuLi occurs at a temperature between about 0° C. and about 20° C.

8. The process of claim 1, wherein the reaction between the nitrile of Formula (III) and $LiCH_2SO_2CH_3$ occurs in a solvent, wherein the solvent is diethyl ether, tetrahydrofuran, N-methylpyrrolidinone, MTBE, glyme, diglyme, toluene, xylene, hexanes, or a combination thereof.

9. The process of claim 1, wherein the reaction between the nitrile of Formula (III) and $LiCH_2SO_2CH_3$ occurs at a temperature between about 0° C. and about 60° C.

10. The process of claim 1, wherein the enamine of Formula (IV) is reduced by $NaBH(OAc)_3$.

11. The process of claim 1, wherein the enamine of Formula (IV) is reduced by $NaBH_4$.

12. The process of claim 1, wherein the reduction of the enamine of Formula (IV) occurs in the presence of an acid, wherein the acid is acetic acid, methanesulfonic acid, trifluoroacetic acid, 4-(trifluoromethyl)benzoic acid, p-toluenesulfonic acid, hydrochloric acid, nitric acid, sulfuric acid, phosphoric acid, or a combination thereof.

13. The process of claim 1, wherein the reduction of the enamine of Formula (IV) occurs in a solvent, wherein the solvent is ethyl acetate, diethyl ether, tetrahydrofuran, acetic acid, acetonitrile, N-methylpyrrolidinone, dimethylformamide, dimethyl sulfoxide, hexanes, or a combination thereof.

14. The process of claim 1, wherein the reduction of the enamine of Formula (IV) occurs at a temperature between about 0° C. and about 25° C.

15. The process of claim 1, wherein the reduction of the enamine of Formula (IV) forms a salt of Formula (I).

16. The process of claim 15, wherein the salt of Formula (I) is hydrolyzed to provide the compound of Formula (I).

17. The process of claim 16, wherein the hydrolysis occurs at a temperature between about 0° C. and about 80° C.

18. The process of claim 16, wherein the hydrolysis occurs in the presence of a base, wherein the base is NaOH, KOH, LiOH, $Ca(OH)_2$, or a combination thereof.

19. The process of claim 16, wherein the hydrolysis occurs in the presence of an acid, wherein the acid is trifluoroacetic acid, 4-(trifluoromethyl)benzoic acid, p-toluenesulfonic acid, methanesulfonic acid, acetic anhydride, a Lewis acid, or a combination thereof.

20. The process of claim 1, wherein $R^1$ and $R^2$ are both ($C_1$-$C_6$)alkoxy.

21. The process of claim 1, wherein $R^1$ and $R^2$ are both ($C_1$-$C_6$)alkyl.

22. The process of claim 1, wherein one of $R^1$ and $R^2$ is ($C_1$-$C_6$)alkoxy, and the other of $R^1$ and $R^2$ is ($C_1$-$C_6$)alkyl.

23. The process of claim 1, wherein $R^1$ is methoxy, and $R^2$ is ethoxy.

24. The process of claim 1, wherein one of $R^1$ and $R^2$ is ($C_1$-$C_6$)alkoxy and the other of $R^1$ and $R^2$ is ($C_3$-$C_6$)cycloalkoxy.

* * * * *